(12) United States Patent
Potyrailo

(10) Patent No.: US 6,500,547 B1
(45) Date of Patent: Dec. 31, 2002

(54) COATING MATERIALS FOR SENSORS AND MONITORING SYSTEMS, METHODS FOR DETECTING USING SENSORS AND MONITORING SYSTEMS

(75) Inventor: Radislav Alexandrovich Potyrailo, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/519,891

(22) Filed: Mar. 6, 2000

(51) Int. Cl.⁷ .......................... G01N 5/00; G01N 30/00
(52) U.S. Cl. ...................... 428/422; 73/31.05; 95/8; 96/413; 96/717; 116/200; 116/206; 422/88; 436/178
(58) Field of Search ................. 116/206, 200; 73/31.05; 96/417, 413; 95/8; 436/178; 422/88; 428/421, 422

(56) References Cited

U.S. PATENT DOCUMENTS

| | | | |
|---|---|---|---|
| 4,530,569 A | 7/1985 | Squire | 350/96.34 |
| 4,681,855 A | 7/1987 | Huang | 436/39 |
| 4,834,496 A * | 5/1989 | Blyler, Jr. et al. | 350/96.29 |
| 4,897,457 A | 1/1990 | Nakamura et al. | 526/247 |
| 4,935,477 A | 6/1990 | Squire | 524/247 |
| 5,151,110 A * | 9/1992 | Bein et al. | 55/75 |
| 5,188,870 A | 2/1993 | Brosig | 428/1.1 |
| 5,201,215 A | 4/1993 | Grqnstaff et al. | 73/54.41 |
| 5,243,539 A | 9/1993 | Holt et al. | 702/30 |
| 5,338,429 A * | 8/1994 | Jolson et al. | 204/415 |
| 5,353,368 A * | 10/1994 | Resnick | 385/145 |
| 5,356,668 A | 10/1994 | Paton et al. | 427/2.25 |
| 5,403,437 A | 4/1995 | Beratan et al. | 156/655 |
| 5,412,750 A | 5/1995 | Nath | 385/125 |
| 5,447,600 A | 9/1995 | Webb | 216/2 |
| 5,468,561 A | 11/1995 | Cho | 428/421 |
| 5,479,430 A | 12/1995 | Shine, Jr. et al. | 372/66 |
| 5,570,447 A | 10/1996 | Liu | 385/125 |
| 5,589,396 A | 12/1996 | Frye et al. | 436/73 |
| 5,604,587 A | 2/1997 | Che et al. | 356/246 |
| 5,661,226 A | 8/1997 | Bowers et al. | 73/24.01 |
| 5,759,625 A | 6/1998 | Laubacher et al. | 427/264 |
| 5,824,603 A | 10/1998 | Cho | 438/725 |
| 5,888,850 A | 3/1999 | Havens et al. | 438/127 |
| 5,910,765 A | 6/1999 | Slemon et al. | 340/517 |
| 5,977,241 A * | 11/1999 | Koloski et al. | 524/502 |
| 6,300,638 B1 * | 10/2001 | Groger et al. | 250/458.1 |

FOREIGN PATENT DOCUMENTS

| | | |
|---|---|---|
| DE | 4424773 | 1/1996 |
| GB | 2226140 | 6/1990 |
| WO | 99/61902 | 12/1999 |

OTHER PUBLICATIONS

Abraham et al., "Characterization of 14 Sorbent Coatings for Chemical Microsensors using a New Solvation Equation", J. Chem. Soc. Perkin Trans., Feb. 1995.*

Alger, Polymer Science Dictionary, pp. 101–102, Apr. 1999.*

Hawley's Condensed Chemical Dictionary, 11$^{th}$ Edition, p. 768, Oct. 1989.*

Ricco, A.J., "SAW Chemical Sensors", Interface, US, Electochemical Society, vol. 3, No. 4, Dec. 21, 1994, pp. 38–44.

Rebiere, D. et al., "Synthesis and evaluation of fluoropolyol isomers as saw microsensor coatings: role of humidity and temperature", Sensors and Actuators B, CH, Elsevier Sequoia S.A., Lausanne, vol. 49, No. 1–2, Jun. 25, 1998, pp. 139–145.

Ozturk, Z.A. et al., Sensors and Actuators B, CH, Elsevier Sequoia S.A., Lausanne, vol. B26, No. 1/03, part 01, May 1, 1995, pp. 208–212.

* cited by examiner

*Primary Examiner*—Paul Thibodeau
*Assistant Examiner*—Ramsey Zacharia
(74) *Attorney, Agent, or Firm*—Noreen C. Johnson; Christian G. Cabou

(57) ABSTRACT

A sensor assembly can detect at least one target material in an environment. The sensor assembly comprises at least one sensor and an amorphous fluoropolymer material coating disposed on a surface of the at least one sensor.

40 Claims, 3 Drawing Sheets

COATING MATERIALS FOR SENSORS AND MONITORING SYSTEMS, METHODS FOR DETECTING USING SENSORS AND MONITORING SYSTEMS

BACKGROUND OF THE INVENTION

The invention relates to coating materials for sensors. In particular, the invention relates to coating materials for chemical sensors.

Sensors generally have varying configurations. Typically, a sensor is provided with a chemically sensitive film (often referred to as a "coating") that is applied onto a surface of the sensor, for example onto a surface of a sensor piezoelectric crystal. Interactions of the film with a material to be detected (hereinafter "target material"), for example an analyte, can induce a change in at least one of mass and visco-elastic properties of the film. This change can be measured as a shift of the resonance frequency of the sensor's crystal. Further, the change may be related to the analyte concentration. For detection of analytes of differing natures, film and analyte interactions include, but are not limited to, hydrogen bonding, stacking, acid-base, electrostatic and size/shape recognition.

The sensor's configuration, materials, and other characteristics vary to define operational characteristics, resonance frequencies, and boundaries for the sensor. For example, differing piezoelectric materials in a sensor substrate operate differently, and thus may define the sensor's operational boundaries and characteristics. If a sensor comprises a quartz crystal microbalance (QCM) as a sensor substrate, the sensor typically operates by propagating mechanical oscillations generally perpendicularly between parallel faces of a thin, quartz-crystal piezoelectric element. If a sensor comprises a surface acoustic wave (SAW) device as a sensor substrate, mechanical oscillations are generally propagated in substantially up-and-down undulations at a radio frequency (RF) along the surface of a thin, piezoelectric element.

The chemically sensitive film, which can be applied to the sensor, may permit the sensor to more readily detect a target material, analyte, or other compound (hereinafter collectively referred to as "target material"), which is not ordinarily sensed by the sensor. The sensitive film often comprises a polymeric material film (hereinafter "polymeric film"). The polymer film changes the response of the sensor by altering the sensor's mechanical oscillation frequencies, and thus permits a target material to be detected by the sensor. The sensor's changing frequencies result from the polymeric film's interaction with the target material. Accordingly, various target materials can be detected by a sensor when the nature of reaction between the polymeric film and target material is known.

A target material usually a vapor, is dissolved (absorbed) into the film, by a process known in the art as "partitioning." The absorbing can change properties of the film. The partition coefficient, K, is a thermodynamic parameter that corresponds to an equilibrium distribution of sorbed molecules between the gas phase and polymeric film. The partition coefficient is ratio of a concentration of target material in the polymeric film, $C_F$, to the concentration of the target material outside of the film, $C_V$. The partition coefficient K is determined according to Equation (1)

$$K=C_F/C_V \quad \text{(Equation 1)}$$

An altered frequency may result from a changed polymeric film mass. An increased film mass lowers a frequency at which the crystal oscillates, including for which it oscillates when exposed to a target material. Thus, the target material perturbs the oscillation of the sensor when the mass of the polymeric film increases, and thus the target material can be detected. The oscillation frequency and mass change of a polymeric film often necessitate that the film be stable, thin, and mechanically rigid. The thin nature of a polymeric film is needed so that the polymeric film's visco-elastic properties, and any changes in those visco-elastic properties produced by partitioning of the target material thereto, do not adversely influence the oscillations of the sensor and therefore provide inaccurate detection of a target material. Further, the polymeric film should be mechanically rigid so the sensor provided with the polymeric film can have repeated sensing applications.

SAW sensor devices coated with thin polymeric material film (known in the art as "chemosensors") have been used as micro-sensors for detecting vapors. The sensitivity to a specific vapor (target material) for such a SAW chemosensor depends on the type, physical and chemical properties, and materials of polymeric film. For example, each of a polymer-vapor partition coefficient, rate of absorption, and desorption processes may influence the operational characteristics of a polymeric film. Exemplary polymeric film materials used as on a SAW chemosensor include, but are not limited to, phenyl-methyl-polysiloxanes, poly(epichlorohydrin), poly (isobutylene), poly(ethylene maleate), and poly (ethylenimine). Some of these materials do not provide stable operations in which controlled, accurate, reliable, and repeated detection operations are possible. Although SAW sensors are typically more sensitive than QCM sensors, the relatively low partition coefficients of polymers used in the past normally preclude the use of SAW and QCM sensors for detection of low concentrations of analytes.

Various film materials may be appropriate for detection of some analytes with selected sensors. One known film for sensors, such as piezoelectric and optical sensors, comprises a vapor-sorbing material. The vapor-sorbing material should enhance detecting capabilities of the sensor, however, a vapor-sorbing material may not possess desired mechanical an/or chemical stability characteristics. Other film materials may be incompatible with sensors, provide inaccurate or unreliable results, and generally be unstable and thus unsuitable for use in some environments.

For example, certain film materials may not provide controlled, accurate, reliable, and repeated detection operations. It is known that some sorbing polymer films may exhibit decreased sensing characteristics, including but not limited to, decreased stability and sensitivity during detection operations, when in contact with certain materials and environments. Further, some sorbing polymer films can decrease sensing operational characteristics upon interactions with neat or aqueous solutions of organic solvents. Furthermore, various sorbing polymer films can decrease sensing operational characteristics upon interactions with alkaline solutions. Moreover, some polymer films are chemically unstable, which means that the polymer film may undergo adverse chemical changes after contact with an analyte or target material. Additionally, some polymer films are mechanically unstable, which means that the polymer film may undergo adverse mechanical characteristic changes after contact with an analyte or target material.

Therefore, a need exists for providing a sensor coating material that can retain desirable sensing characteristics if in contact with certain materials and environments. Further, a need exists for a sensor coating material that can provide stable detection operations in which controlled, accurate, reliable, and repeated detection operations are possible if in contact with certain materials and environments.

SUMMARY OF THE INVENTION

Accordingly, the invention sets forth a sensor assembly that can detect at least one target material in an environment. The sensor assembly comprises at least one sensor and an amorphous fluoropolymer material coating disposed on a surface of the at least one sensor.

Another aspect of the invention comprises a method for detecting at least one target material. The method comprises: providing at least one sensor; disposing an amorphous fluoropolymer material coating on the at least one sensor to form at least one coated sensor; disposing the at least one coated sensor in an environment that may contain at least one target material, whereby the amorphous fluoropolymer material coating of the coated sensor undergoes changes in response to interactions with the target materials dependent on concentrations of the target material; and relating the changes in the amorphous fluoropolymer material coating to the target material concentration.

A further aspect of the invention provides a monitoring system for at least one of detection, analysis, and evaluation of a target material in an environment. The monitoring system comprises at least one sensor; an amorphous fluoropolymer material coating disposed on a surface of the at least one sensor; and a device that analyzes and evaluates a change in the amorphous fluoropolymer material coating due to interactions with the target material.

In another aspect of the invention, a monitoring system is provided for at least one of detection, analysis, and evaluation of a target material in an environment. The monitoring system comprises means for sensing a target material in an environment; an amorphous fluoropolymer material coating disposed on a surface of the means for sensing; and means for analyzing and evaluating a change in the amorphous fluoropolymer material coating due to interactions with the target material.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF THE INVENTION

Figure 1:
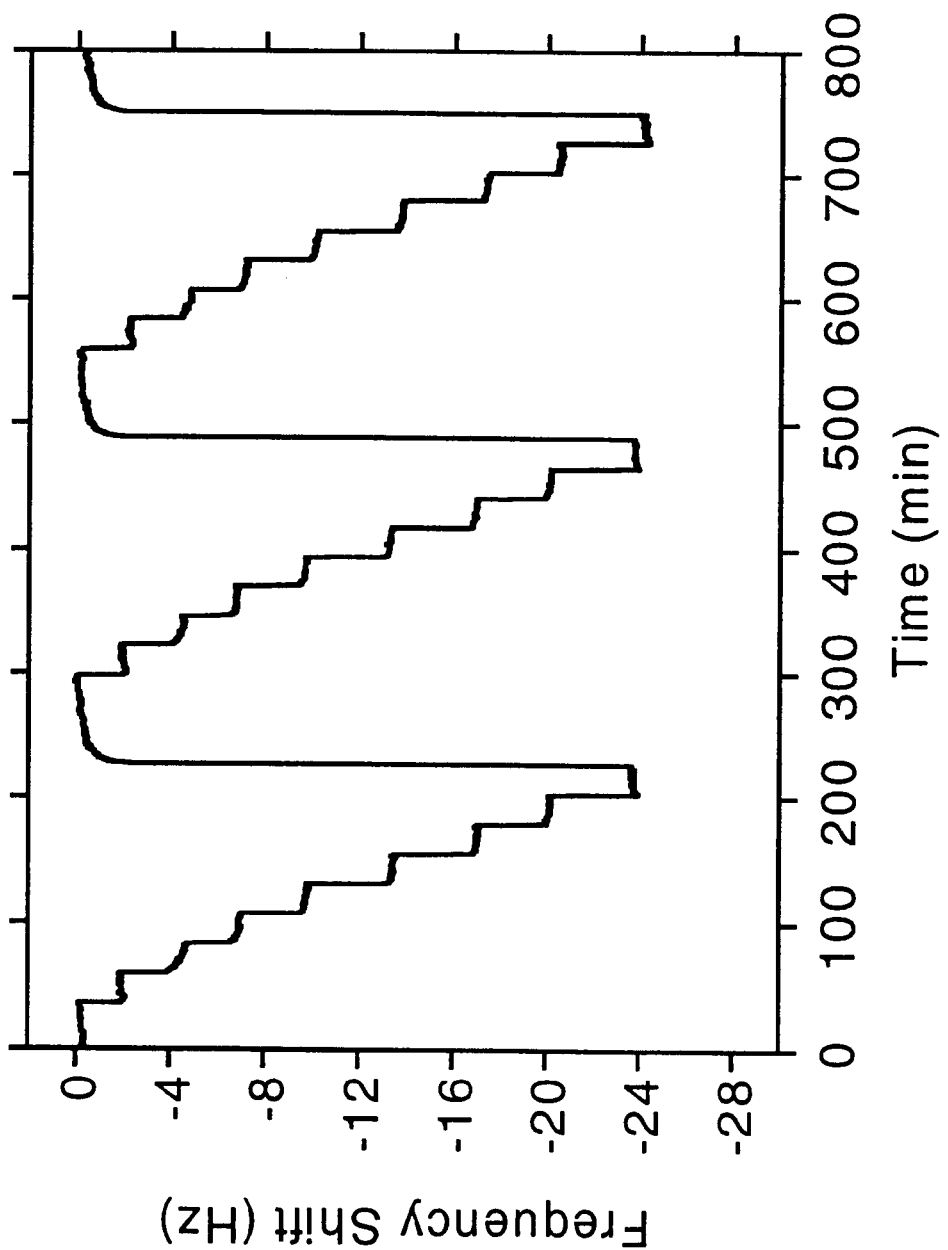
FIG. 1 is a graph of frequency shift versus time in dynamic responses during exposure of a quartz crystal microbalance (QCM) sensor that comprises Teflon AF2400 coating to varying trichloroethylene (TCE) concentration, in which the TCE :concentrations are at about 0, 10, 21, 30, 42, 56, 71, 83, and 100 ppm.

Sensors comprising amorphous fluoropolymer materials as sensor coating materials are provided by the invention. The sensors that are provided with the amorphous fluoropolymer material coatings comprise, but are not limited to, surface acoustic wave (SAW) sensors, quartz crystal microbalance (QCM) sensors, and combinations thereof. The combinations of sensors comprise sensor arrays, such as, but not limited to, sensor arrays comprising a plurality of one type of sensor and sensor arrays comprising a plurality of different types of sensors. In the following description of the invention, reference will be made to a "sensor assembly" that includes a single sensor or a sensor array that comprises any number of sensors, wherein the sensors can be of different sensor types.

The amorphous fluoropolymer material coatings, as embodied by the invention, can comprise amorphous copolymers of perfluoro-2,2-dimethyl-1,3-dioxole. These amorphous copolymers are known for use in stick reducing agents in micromechanical devices, fluorinating polyester fabrics, protective coatings on electronic packages and solid state lasers, and enhancement resolution for liquid crystal displays.

Alternatively, the amorphous fluoropolymer material coatings, as embodied by the invention, may comprise random copolymers of tetrafluoroethylene (TEF) (also known as Telfon™) and perfluoro-2,2-dimethyl-1,3-dioxole (PDD).

Amorphous fluoropolymer materials for sensor assembly coatings may also comprise amorphous terpolymers of PDD and TEF, and another comonomer. The comonomer can comprise, but is not limited to, at least one of perfluoroolefins and perfluoro(alkyl vinyl esters). Further amorphous fluoropolymer coating materials may comprise dipolymers and terpolymers (collectively referred to as "copolymers") of PDD with comonomers, which can comprise perfluoroolefins and perfluoro(alkyl vinyl ethers).

Alternatively, the amorphous fluoropolymer materials for the sensor assembly, as embodied by the invention, can comprise amorphous homopolymers and copolymers, which contain repeating cyclic structures formed during a cyclic polymerization of perfluoro(butenyl vinyl ether) (PBVE). These amorphous fluoropolymer materials exhibit enhanced mechanical and chemical stability when exposed to at least one of organic solvents and alkaline solutions. Thus, the amorphous fluoropolymer material coatings comprising amorphous homopolymers and copolymers, which contain repeating cyclic structures, comprise desirable sensor assembly coatings. These coatings are useful in for chemical sensor assemblies as they are chemically and mechanically resistant in adverse environments.

The amorphous fluoropolymer material coatings in sensor assemblies provide a stable coating, in which the coating is mechanically and chemically stable for detection operations. Sensor assemblies comprising the amorphous fluoropolymer material coatings are generally mechanically and chemically stable upon exposure to nonpolar solvents. This mechanically and chemically stability is contrary to known sorbing materials, such as conventional polymeric films that are provided as coatings on chemical sensors in which they can be dissolved by contact with certain environments. These dissolving environments include, but are not limited to, environments comprising nonpolar solvents. Therefore, the amorphous fluoropolymer material coatings on a sensor assembly, as embodied by the invention, can provide a robust coating for a sensor assembly, such as but not limited to, chemical sensor assemblies.

The sorption properties of amorphous fluoropolymer material coatings to different molecular weight analytes may vary. The sorption property variation may be a function of the amorphous fluoropolymer material coating's fluoropolymer composition. The sorption property variation makes these amorphous fluoropolymer materials a desirable coating material because the arrangement of the different sensors into a sensor array provides diversity in sorption characteristics in the sensor array. The diversity in sorption characteristics can result in the sensor array being capable of being tuned or discriminating between multiple analytes and target materials.

The amorphous fluoropolymer material coatings on a sensor assembly, as embodied by the invention, can permit the sensor assembly to detect various analyte and target materials. The sensor assembly, as embodied by the invention, can be connected to monitoring system that provides near real-time or real-time system for at least one of detection, analysis, and evaluation. The terms "real-time" and "near real-time" mean that any delays from the time of detecting and sensing and the results being made available are minimal. For example, the delays may be on the order of minutes, and possibly a few seconds, or longer. The delay period may vary as long as the information is considered relevant and of value to the interested party, regardless of the delay. Also, the term real time can mean the time required for a user of the sensor assembly to obtain the detection information as long as it is desired by the user. In the following description of the invention, the term "real-time" will be used, and it should be construed as including both "near real-time" and "real-time".

The detection information, either in its as-detected state or in its analyzed and evaluated state, can be provided by the monitoring system to parties who may desire and benefit from the information. These parties include, but are not limited to, regulatory agencies, manufacturing entities who can operate the sensor assembly, as embodied by the invention, service centers who can provide alerts concerning the detected information for example in case of detection of a preset level of target materials, and other such parties. The information can be provided to parties over a communications link. The communications link is selected from, at least one of a phone modem, network connection, communication, radio communication and other wireless communication systems, cellular communication, satellite communication, web access communication, and Internet access communication, and combinations thereof.

The amorphous fluoropolymer material coatings can be used with systems for the detection, analysis, and evaluation of various analytes and target materials, in which the term "target material" generally refers to an analyte material. The sensor assembly with amorphous fluoropolymer material coatings, as embodied by the invention, can be used for in conjunction with a system that allows at least one of real-time detection, analysis, and evaluation of target materials. The amorphous fluoropolymer material coatings can also be used for quantification of target materials. The target materials, within the scope of the invention, can comprise volatile compounds, in which the volatile materials may be vaporous compounds that can be found in at least one of air, groundwater, and bodies of water, such as but limited to, lakes, ponds, streams, rivers, and oceans. Exemplary target materials that can be detected by a sensor assembly with an amorphous fluoropolymer material coating, as embodied by the invention, comprise: toluene, tetrachloroethylene (PCE), trichloroethylene (TCE), vinyl chloride (VC), and three isomers of dichloroethylene (DCE): cis-1,2-DCE, trans-1,2-DCE, and 1,1-DCE. The following description of the invention may refer to an analyte as the target material, however, this description is not intended to limit the invention in any manner.

Exemplary volatile compounds, within the scope of the invention, comprise, but are not limited to, halogenated hydrocarbons. The halogenated hydrocarbons comprise, but are not limited to, chlorinated hydrocarbons and chlorinated solvents (hereinafter collectively referred to as "chlorinated solvents"). Chlorinated solvents are commonly used as chemical carriers, solvents, paint removers, and cleaners. Chlorinated solvents have low flammability and are fairly stable, both chemically and biologically. Chlorinated solvents are also used as intermediates in chemical manufacturing and as carrier solvents for pesticides and herbicides.

Sensor assemblies with amorphous fluoropolymer material coatings can sense and detect analytes based on interactions of the amorphous fluoropolymer materials in the coating and analytes. For example, a sensor assembly with an amorphous fluoropolymer material coating may be disposed in an environment for detection of an analyte concentration or concentrations of multiple analytes in a mixture. Properties of the amorphous fluoropolymer material coating may undergo changes as a function of analyte concentration or multiple analytes concentrations. The property change can be a change the amorphous fluoropolymer material coating mass, change of amorphous fluoropolymer material coating visco-elastic properties, or other mechanical property changes. Alternatively, the amorphous fluoropolymer material coating may undergo changes in dielectric and optical properties, as a function of analyte concentration.

Optical properties of the amorphous fluoropolymer material coating may also be changed by partitioning of an analyte into the amorphous fluoropolymer material coating. The partitioning can be monitored as a change in at least one of absorbance, scattering, refractive index, and luminescence of the amorphous fluoropolymer material.

Alternatively, a dye, such as, but not limited to, a chemically sensitive dye, that is incorporated into an amorphous fluoropolymer material coating for a sensor assembly. Thus, a dye molecule can then be directly attached to the amorphous fluoropolymer molecule. Accordingly, changes of the optical properties of the dye upon exposure of the amorphous fluoropolymer material coating to an analyte can be related to an analyte concentration and any variations thereof in the exposed environment.

The amorphous fluoropolymer material coatings may be deposited onto a sensor assembly surface by any appropriate deposition process. For example, and in no way limiting of the invention, amorphous fluoropolymers can be dissolved in a solvent, such as, perfluoro(2-butyl tetrahydrofuran) to form an amorphous fluoropolymer material polymer solution. Thin films of the formed-amorphous fluoropolymer material polymer solution can then be deposited onto a sensor assembly surface. The depositing of the amorphous fluoropolymer material polymer solution can be conducted by at least one of: dip-coating, spin-coating, spraying, brushing, and combinations thereof, and other deposition processes.

The TEF/PDD ratio of coating materials can be controlled to influence and tune the chemical sorption property of amorphous fluoropolymer material coatings, as embodied by the invention. Amorphous fluoropolymer material coatings for sensor assemblies that comprise differing TEF/PDD ratios may be useful for sensor array applications. In such sensor array applications, each sensor of the sensor array may comprise a different amorphous fluoropolymer material coating. Each amorphous fluoropolymer coating material coating can be tuned for different target materials to be detected. Therefore, a sensor array thus provided can detect various target materials.

A sensor array that comprises amorphous fluoropolymer material coatings, as embodied by the invention, may comprise differing amorphous fluoropolymer materials of a similar amorphous fluoropolymer class on sensors in the sensor array. The term "similar" means that the amorphous fluoropolymer materials are within the polymer class including TEF/PDD polymers. For example, but not limiting the invention, different amorphous fluoropolymer materials from a similar amorphous fluoropolymer class can be applied on each unit of a sensor array. Exemplary units of a sensor array may comprise transducers that form the sensor array. In such a sensor array configuration, selective analyte detection, for example analyte detection in complex mixtures, can be conducted by the monitoring system analyzing a sensor array response pattern. A reading of the sensor array response pattern may be conducted by appropriate response pattern recognition techniques in the monitoring system. These techniques include evaluation and analyzing in near real-time or real-time.

Detection operations of a sensor assembly comprising amorphous fluoropolymer material coatings, as embodied by the invention, were investigated, and results of the investigation are set forth below. A sensor assembly is prepared by applying amorphous fluoropolymer material coatings as a thin film onto a surface of a quartz crystal microbalance (QCM) sensor. These quartz crystals typically oscillate in a thickness-shear mode with a fundamental frequency of about 10 MHz, as described above. The sensor assembly substrate comprises an AT-cut quartz crystal comprising gold electrodes.

The amorphous fluoropolymer material coating is deposited on the sensor by a film deposition process. The film deposition process comprises dissolving amorphous fluoropolymers in perfluoro(2-butyl tetrahydrofuran) (fluorinert, electronic liquid FC-75, produced by 3M Company) to form a polymer solution. The polymer solution is applied to surfaces of QCM sensors and dried to form amorphous fluoropolymer coated QCM sensors.

The amorphous fluoropolymer coated QCM sensors (hereinafter "coated sensor") are then arranged in a low-dead volume flow-through gas cell. The coated sensor is monitored for changes in amorphous fluoropolymer mass upon exposure of the coated sensor to analyte vapors. A resonant oscillation frequency of the coated sensor is monitored as a function of analyte concentration in a gas mixture in the gas cell. Sensor assembly performance is then evaluated with respect to several analyte vapors. These analyte vapors, include: toluene, tetrachloroethylene (PCE), trichloroethylene (TCE), vinyl chloride (VC), and three isomers of dichloroethylene (DCE): cis-1,2-DCE, trans-1,2-DCE, and 1,1-DCE. These vapors are provided at concentrations of about 106 ppm (PCE), about 100 ppm (TCE), about 101 ppm (cis-1,2-DCE), about 99 ppm (trans-1,2-DCE), about 102 ppm (1,1-DCE), about 100 ppm (VC), and about 98 ppm (toluene) in air, respectively. The vapor's concentrations are generated by diluting analyte vapors with dry nitrogen gas. A gas flow of the analyte vapors is kept essentially constant at about 480 $cm^3$ $min^{-1}$ using known mass-flow controllers.

Next, the sorption properties of amorphous fluoropolymer material coatings are then investigated with respect to vapors of chlorinated solvents to evaluate the sorption properties of amorphous fluoropolymer material coatings. A quartz crystal is coated with an amorphous fluoropolymer material coating, which comprises Teflon AF2400. The thickness of the amorphous fluoropolymer material coating is measured as a shift of a fundamental oscillation frequency of the crystal, and was determined to be about 74 kHz. The measurements are performed at about 20° C. Upon exposure of the coated sensor to varying concentrations of vapors, a change in sensor response or signal can be recorded. Sensor response is observed to be essentially reversible and rapid, for example occurring in less than about a minute. This sensor response characteristic may indicate desirable rapid sorption and desorption characteristics of the amorphous fluoropolymer material, as embodied by the invention.

Figure 2:
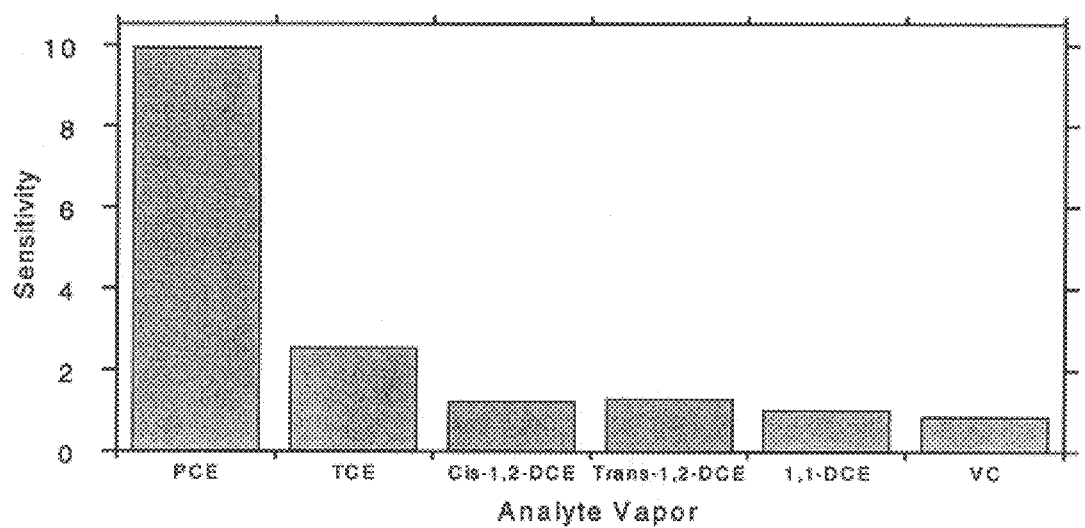
FIG. 2 is a chart of mass sensitivity for various analyte vapors during exposure of a QCM sensor to different analyte vapors, each at 10 ppm, with the QCM sensor comprising a tetrafluoroethylene (Teflon AF2400) coating, in which sensitivity is estimated in hertz (Hz) response that has been normalized by a 100-kHz thick film.

FIG. 1 is an exemplary graph of frequency shift versus time in dynamic responses during exposure of the coated QCM sensor, as described above, to varying TCE concentration. FIG. 1 illustrates an exemplary dynamic response of a sensor, as embodied by the invention. The TCE concentrations are at about 0, 10, 21, 30, 42, 56, 71, 83, and 100 ppm. FIG. 2 is a chart of mass sensitivity for various analyte vapors during exposure of a QCM sensor to different analyte vapors, each at 10 ppm, with the QCM sensor comprising a Teflon AF2400 coating, in which sensitivity is estimated in hertz (Hz) response that has been normalized by a 100-kHz thick film A sensor mass sensitivity is evaluated as a function of analyte, as provided in Table 1 and FIGS. 1 and 2. The data provided in Table 1 comprises estimated mass sensitivity in Hz response, which is normalized by about a 100-kHz thick coating that has been exposed to about 10 ppm of a target material in the form of a vapor.

TABLE 1

| SENSOR MASS SENSITIVITY | |
|---|---|
| Analyte Vapor | Sensitivity |
| PCE | 9.93 |
| TCE | 2.54 |
| Cis-1,2-DCE | 1.23 |
| Trans-1,2-DCE | 1.29 |
| 1,1-DCE | 1.02 |
| VC | 0.86 |

A further investigation with regard to a sensor array in which each sensor of the array comprises an amorphous fluoropolymer material coating. A four-sensor array is constructed for evaluating amorphous fluoropolymers capability to discriminate between organic vapors. The amorphous fluoropolymer material coating comprises Teflon AF 1600, which is disposed on two crystals. The amorphous fluoropolymer material coatings are about 123 kHz thick and about 153 kHz thick, as described above. Additionally, the crystals of two other sensors are coated with amorphous fluoropolymer material coatings that comprise Teflon AF 2400, in which the coatings comprise a thickness of about 74 kHz and about 356 kHz. Different concentrations of target materials, toluene and TCE, are introduced into the sensor array, in which the sensor array is kept at a temperature of about 10° C.

Figure 3:
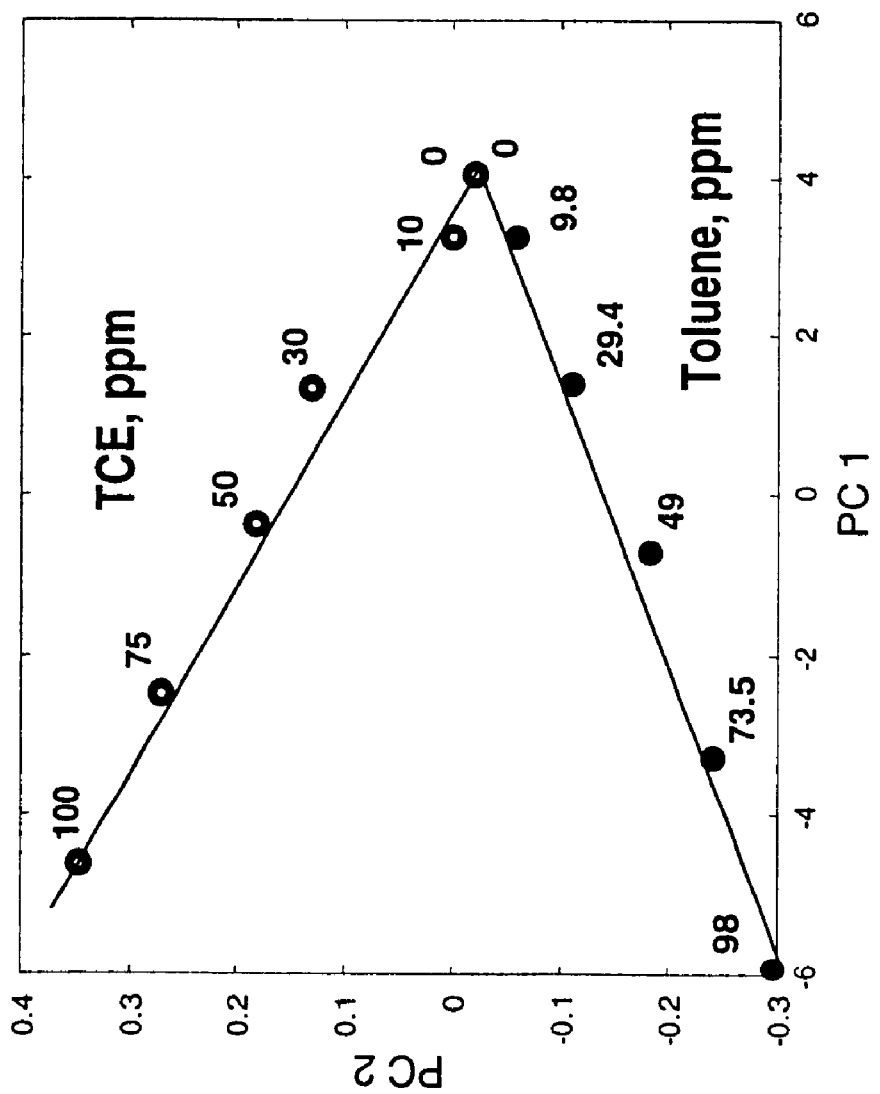
FIG. 3 is a graph illustrating discrimination for principle components analysis (PCA) between differing concentrations of toluene and TCE vapors in a QCM sensor array that comprises sensors comprising tetrafluoroethylene (Teflon AF1600 and Teflon AF2400) coatings.

The detected information is collected as a concentration-sensor response matrix for each sensor of the sensor array, as embodied by the invention. An analysis of detected information is performed with principal components analysis (PCA) devices and tools, such as PLS Toolbox (Version 2.0, Eigenvector Research, Inc., Manson, Wash.) that is operated with Matlab software (Version 5.3, The Mathworks Inc., Natick, Mass.). These devices and tools are merely exemplary of the devices and tools within the scope of the invention, and other such principal component analysis devices and tools can be used. For analysis, the collected information is autoscaled, and the first two principal components are selected and plotted, as in FIG. 3. As illustrated in FIG. 3, more than about 95% variance in the detection capability of the sensor array comprising the amorphous fluoropolymer material coatings, as embodied by the invention, can be captured by PCA devices and tools. FIG. 3 illustrated that toluene and TCE vapors can be separated from each other using appropriate PCA devices and tools. FIG. 3 also illustrates a correspondence between vapor concentration of the analyte and the discrimination ability of a sensor assembly, in which an increase in vapor concentration corresponds to an increase in the discrimination ability of a sensor, as embodied by the invention.

Another investigation was conducted to evaluate environmental stability of the chemically sensitive amorphous fluoropolymer material coatings. The amorphous fluoropolymer material coatings are chemically and mechanically stable upon direct contact with aggressive solvents. These solvents include, but are not limited to: solvents used for dissolving of polymers, for example chloroform; solvents used as gasoline simulators, for example hexane and toluene in a 9:1 ratio mixture; and alkaline solvent, for example ammonium hydroxide that decomposes room-temperature vulcanizable (RTV) silicone films. Table 2 summarizes the environmental stability of amorphous fluoropolymer material coatings, as embodied by the invention. The chemical and mechanical stability of the amorphous fluoropolymer material coatings is unlike conventional polymer films, which are typically mechanically or chemically unstable. The amorphous fluoropolymer material coatings, as embodied by the invention, that are deposited onto a surface of a quartz crystal have been experimentally determined to be removed only by applying a solvent comprising perfluoro(2-butyl tetrahydrofuran) (fluorinert, electronic liquid FC-75, 3M Company).

TABLE 2

ENVIRONMENTAL STABILITY OF AMORPHOUS FLUOROPOLYMER FILMS

| Solvent | Film performance |
| --- | --- |
| Hexane/toluene mixture, 9:1 ratio | Stable |
| Chloroform | Stable |
| Ammonium hydroxide | Stable |
| Methanol | Stable |
| Acetone | Stable |
| Perfluoro(2-butyl tetrahydrofuran) | Dissolved |

While various embodiments are described herein, it will be appreciated from the specification that various combinations of elements, variations or improvements therein may be made by those skilled in the art, and are within the scope of the invention.

I claim:

1. An acoustic wave sensor assembly for detecting and quantifying at least one target material, the sensor assembly comprising:
   at least one acoustic wave sensor; and
   an amorphous fluoropolymer coating comprising tetrafluoroethylene (TEF) and perfluoro-2,2-dimethyl-1,3-dioxole (PDD) disposed on a surface of the at least one sensor wherein the coating causes a signal change in relation to the concentration of at least one target material, wherein the coating simultaneously performs a function of a chemically sensitive layer and a protective layer.

2. A sensor assembly according to claim 1, wherein the at least one sensor consists of one sensor.

3. A sensor assembly according to claim 1, wherein the at least one sensor comprises a sensor array, the sensor array comprising a plurality of sensors.

4. A sensor assembly according to claim 1, wherein the at least one coated sensor comprises at least one of a surface acoustic wave (SAW) sensor or a quartz crystal microbalance (QCM) sensor.

5. A sensor assembly according to claim 1, wherein the at least one target material comprises an analyte.

6. A sensor assembly according to claim 1, wherein the at least one target material comprises toluene, tetrachloroethylene (PCE), trichloroethylene (TCE), vinyl chloride (VC), and isomers of dichloroethylene (DCE) selected from cis-1,2-DCE, trans-1,2-DCE, and 1,1-DCE.

7. A sensor assembly according to claim 1, wherein the at least one target material comprises halogenated hydrocarbons.

8. A sensor assembly according to claim 1, wherein the at least one target material comprises chlorinated hydrocarbons and chlorinated solvents.

9. A sensor assembly according to claim 1, wherein the coating comprises an amorphous copolymer of perfluoro-2,2-dimethyl-1,3-dioxole PDD and tetrafluoroethylene (TEF).

10. A sensor assembly according to claim 9, wherein the coating further comprises an amorphous terpolymer of tetrafluoroethylene (TEF), perfluoro-2,2-dimethyl-1,3-dixole (PDD), and a third monomer wherein the third monomer comprises a perfluoroolefin or a perfluoro(alkyl vinyl ester).

11. A sensor assembly according to claim 9, wherein the coating further comprises an additional copolymer of perfluoro-2,2-dimethyl-1,3-dioxole (PDD) and a comonomer selected from perfluoroolefins and perfluoro(alkyl vinyl ethers).

12. A sensor assembly according to claim 9, wherein the coating further comprises at least one homopolymer and/or an additional copolymer, wherein the homopolymer comprises repeating cyclic structures formed during cyclic polymerization of perfluoro(butenyl vinyl ether) (PBVE) and the additional copolymer comprises repeating cyclic structures formed during cyclic polymerization of perfluoro(butenyl vinyl ether) (PBVE) with at least one other monomer.

13. A sensor assembly according to claim 1, wherein the coating comprises sorption properties that vary upon interactions with target materials comprising different molecular weights.

14. A sensor assembly according to claim 1, wherein the coating undergoes a property change as a function of interactions with the target material, the interactions being dependent of target material concentration.

15. A sensor assembly according to claim 1, wherein the property change of the coating as a function of target material concentration comprises at least one of: an optical property change of the coating; a mass change of the coating; a visco-electric property change of coating; and mechanical property changes of the coating.

16. A sensor assembly according to claim 1, wherein the coating further comprises a dye.

17. A sensor assembly according to claim 16, wherein dye is incorporated into a fluoropolymer molecule of the coating.

18. A sensor assembly according to claim 16, wherein the dye and the coating undergoes optical property changes as a function of interactions with target materials.

19. A sensor assembly according to claim 1, wherein the target material comprises a target material in at least one of: groundwater, air, and bodies of water.

20. A sensor assembly according to claim 1, further comprising a monitoring system in cooperation with the sensor assembly, the sensor assembly and monitoring system providing at least one of detection, evaluation, and analysis of the target material.

21. A sensor assembly according to claim 1, wherein the sensor assembly and monitoring system provide at least one of real-time and near real-time detection, evaluation, and analysis of the target material.

22. A sensor assembly according to claim 1, wherein the coating is disposed on the sensor assembly by a film deposition process.

23. A method for detecting and quantifying at least one target material, the method comprising:

providing at least one acoustic wave sensor;

disposing an amorphous fluoropolymer coating comprising tetrafluoroethylene (TEF) and perfluoro-2,2-dimethyl-1,3-diolxole (PDD) on the at least one sensor to form at least one coated sensor wherein the coating causes a signal change in relation to the concentration of at least one target material, wherein the coating simultaneously performs a function of a chemically sensitive layer and a protective layer;

disposing the at least one coated sensor in an environment, the environment may contain at least one target material, whereby the coating of the coated sensor undergoes changes in response to interactions with the target materials; and relating the changes in the coating to the target material concentration.

24. A method according to claim 23, wherein the step of disposing the at least one coated sensor in an environment comprises disposing the coated sensor in at least one of groundwater, air, and bodies of water.

25. A method according to claim 23, wherein the step of disposing the coating on the at least one sensor to form at least one coated sensor comprises film deposition.

26. A method according to claim 23, wherein the coating is selected from: an amorphous copolymer of perfluoro-2,2-dimethyl-1,3-dioxole (PDD) and tetrafluoroethylene (TEF); a random copolymer of tetrafluoroethylene (TEF) and perfluoro-2,2-dimethyl-1,3-dioxole (PDD); an amorphous terpolymer of tetrafluoroethylene (TEF) and perfluoro-2,2-dimethyl-1,3-dioxole (PDD) wherein the third monomer comprises a perfluoroolefin or a perfluoro(alkyl vinyl ester); an amorphous copolymer of perfluoro-2,2-dimethyl-1,3-dioxole (PDD) and tetrafluoroethylene (TEF) and an additional copolymer comprising perfluoro-2,2-dimethyl-1,3-dioxole (PDD) and a comonomer selected from perfluoroolefins and perfluoro(alkyl vinyl ethers); an amorphous copolymer of perfluoro,-2,2-dimethyl-1,3-dioxole (PDD) and tetrafluoroethylene (TEF) and at least one homopolymer and/or one additional copolymer, wherein the homopolymer comprises repeating cyclic structures formed during cyclic polymerization of perfluoro(butenyl vinyl ether) (PBVE) and the additional copolymer comprises repeating cyclic structures formed during cyclic polymerization of perfluoro(butenyl vinyl ether) (PBVE) with at least one other monomer.

27. A method according to claim 23, wherein the target material comprises at least one target material selected from: toluene, tetrachloroethylene (PCE), trichloroethylene (TCE), vinyl chloride (VC), and isomers of dichloroethylene (DCE) selected from cis-1,2-DCE, trans-1,2-DCE, and 1,1-DCE.

28. A method according to claim 23, wherein the target material comprises halogenated hydrocarbons.

29. A method according to claim 23, wherein the target material comprises chlorinated hydrocarbons and chlorinated solvents.

30. A method according to claim 29, wherein the step of relating can provide at least one of real-time and near real-time detection, evaluation, and analysis of the target material.

31. A monitoring system for at least one of detection, analysis, and evaluation of a target material in an environment; the monitoring system comprising:

at least two acoustic wave sensors;

an amorphous fluoropolymer coating comprising tetrafluoroethylene (TEF) and perfluoro-2,2-dimethyl-1,3-dioxole (PDD) disposed on a surface of each sensor wherein the coating causes a signal change in relation to the concentration of at least two target materials, wherein the coating simultaneously performs a function of a chemically sensitive layer and a protective layer; and a device that analyses and evaluates a change in the coating due to interactions with the target material, wherein the change is evaluated using concentration-sensor response matrix analysis.

32. A monitoring system according to claim 31, wherein the change of the coating due interactions with the target material comprise at least one of: an optical property change of the coating; a mass change of the coating; a visco-electric property change of the coating; and mechanical property changes of coating.

33. A monitoring system according to claim 31, wherein the device can provide at least one of real-time and near real-time detection, analysis, and evaluation of the target material.

34. A monitoring system according to claim 33, wherein the device provides information to parties over a communications link.

35. A monitoring system according to claim 34, wherein the communications link is selected from, at least one of a phone modem, network connection, communication, radio communication and other wireless communication systems, cellular communication, satellite communication, web access communication, and Internet access communication, and combinations thereof.

36. A monitoring system according to claim 34, wherein the communications link is selected from, at least one of a phone modem, network connection, communication, radio communication and other wireless communication systems, cellular communication, satellite communication, web access communication, and Internet access communication, and combinations thereof.

37. A monitoring system for at least one of detection, analysis, and evaluation of a target material in an environment; the monitoring system comprising:

means for acoustic wave sensing of a target material in an environment;

an amorphous fluoropolymer coating comprising tetrafluoroethylene (TEF) and perfluoro-2,2-dimethyl-1,3-dioxole (PDD) disposed on the surface of the means for sensing wherein the coating causes a signal change in relation to the concentration of at least one target material, wherein the coating simultaneously performs a function of a chemically sensitive layer and a protective layer; and means for analyzing and evaluating a change in the coating due to interactions with the target material.

38. A monitoring system according to claim 37, wherein the means for means for analyzing and evaluating can provide at least one of real-time and near real-time detection, analysis, and evaluation of the target material.

39. A monitoring system according to claim 38, wherein the means for analyzing and evaluating provides information to parties over a communications link.

40. A sensor assembly for detection of target materials, the sensor assembly comprising:

a quartz crystal microbalance (QCM) sensor, the sensor comprising a quartz substrate, the quartz substrate comprises an AT-cut quartz crystal and gold electrodes;

an amorphous fluoropolymer material coating disposed on the quartz crystal microbalance (QCM) sensor, the amorphous fluoropolymer material coating comprising a thin layer having thickness-shear mode with a fundamental frequency of about 10 MHz.

* * * * *